(12) United States Patent
Chutjian et al.

(10) Patent No.: US 8,116,981 B2
(45) Date of Patent: Feb. 14, 2012

(54) DETECTOR USING MASS SPECTROSCOPY FOR CHARACTERIZATION OF BIOLOGICAL COMMUNITY

(75) Inventors: Ara Chutjian, La Crescenta, CA (US); Murray R. Darrach, Valencia, CA (US); Roger G. Kern, Alhambra, CA (US)

(73) Assignee: California Institute of Technology, Pasadena, CA (US)

( * ) Notice: Subject to any disclaimer, the term of this patent is extended or adjusted under 35 U.S.C. 154(b) by 839 days.

(21) Appl. No.: 10/447,674

(22) Filed: May 28, 2003

(65) Prior Publication Data

US 2004/0049107 A1  Mar. 11, 2004

Related U.S. Application Data

(60) Provisional application No. 60/383,904, filed on May 28, 2002.

(51) Int. Cl.
*G01N 33/48* (2006.01)
*B01D 59/44* (2006.01)

(52) U.S. Cl. ......................................... 702/19; 250/307

(58) Field of Classification Search ............... 702/19
See application file for complete search history.

(56) References Cited

U.S. PATENT DOCUMENTS

| | | | | |
|---|---|---|---|---|
| 4,933,551 A | * | 6/1990 | Bernius et al. | 250/288 |
| 5,374,828 A | * | 12/1994 | Boumsellek et al. | 250/427 |
| 6,017,693 A | * | 1/2000 | Yates et al. | 435/5 |
| 6,022,540 A | * | 2/2000 | Bruder et al. | 424/133.1 |
| 6,469,299 B2 | | 10/2002 | Chutjian et al. | |
| 6,521,898 B2 | | 2/2003 | Chutjian et al. | |
| 6,583,702 B2 | | 6/2003 | Chutjian et al. | |
| 2003/0077840 A1 | | 4/2003 | Chait et al. | |

OTHER PUBLICATIONS

Chalmers et al. "Theoretical Analysis of Cell Separation Based on Cell Surface Marker Density," Biotechnology and Bioengineering, vol. 59 (1998) pp. 10-20.*
Abstract from Alomirah et al. "Application of mass spectrometry to food proteins and peptides," Journal of Chromotography, vol. 893 (2000), pp. 1-21.*
Kelly et al., "Electrospray Analysis of Proteins: a Comparison of Positive-ion and Negative-ion Mass Spectra at High and Low pH," Organic Mass Spectrometry, vol. 27 (1992) pp. 1143-1147.*
Bruins, "Mechanistic aspects of electrospray ionizaiton," Journal of Chromatography: A, vol. 794 (1998) pp. 345-357.*
Pinnaduwage et al. et al., "Enchanced electron attachment to superexcited states of saturated tertiary amines," J. Chem. Phys., vol. 95 (1991) pp. 274-287.*

* cited by examiner

*Primary Examiner* — Marjorie Moran
*Assistant Examiner* — Anna Skibinsky
(74) *Attorney, Agent, or Firm* — Perkins Coie LLP

(57) ABSTRACT

Provided are methods and systems for rapidly and effectively characterizing a cell as belonging to a particular genus, species, strain, or having a particular phenotype. The methods and systems utilize mass spectrometry and low-energy negative ionization to detect cell surface markers indicative of a particular cell.

13 Claims, 4 Drawing Sheets

US 8,116,981 B2

DETECTOR USING MASS SPECTROSCOPY FOR CHARACTERIZATION OF BIOLOGICAL COMMUNITY

CROSS REFERENCE TO RELATED APPLICATIONS

The present application claims the benefit of priority under 35 U.S.C. §119 to provisional application Ser. No. 60/383,904, filed May 28, 2002, the disclosure of which is incorporated herein by reference.

TECHNICAL FIELD

This invention relates to low-energy ionization techniques, and more particularly to methods and, systems for characterizing a cell in a biological sample.

BACKGROUND

Methods and systems for detecting and characterizing cell-types, both in terms of the number of a particular cell-type and the type of single cellular organism, as well as the cell's phenotype are needed. Methods and instruments that can rapidly identify cell-types and numbers of a particular cell-type in a biological sample could be useful in medical diagnosis, food monitoring, and environmental sampling.

Current methods of identifying cells include the use of PCR techniques, antibodies, and various culture conditions. For example, current methods of identifying bacterial cells include culturing the cells in a desired medium. Such techniques are often time consuming and inadequate. For example, there must be some a priori knowledge of what biological species are being cultured in order to provide the correct growth medium; growing a colony may also take up to a day and consume expendibles, one must subsequently dispose of the cultured colony to avoid hazard to the environment. This disposal process itself constitutes a risk to the environment.

Several techniques are currently proposed or in development at other laboratories for microbial detection. These include UV fluorescence, UV resonance Raman spectroscopy, and the use of optimal DNA probes for simultaneous capture, amplification, and fluorescence-detection of several bacterial types. While the UV fluorescence and resonance-Raman methods are conceptually simple, they appear to have limited specificity and sensitivity. The UV fluorescence spectra of many bacteria are similar and hence one must appeal to pattern-recognition algorithms for identifying the quantifying microorganisms at the aggregate, genus, and species level. The data processing requires a high signal-to-background in the spectra, thus relatively high organism densities ($10^3$-$10^4$ colony forming units (CFUs) in the field of view of the excitation source), resulting in limited sensitivity, in addition to a reduced probability of detection (the detector system must be rastered over a large field of view in order to chance upon the micro-organism). Similar effects arise in UV resonance Raman spectroscopy. Raman signatures and shifts can also depend on bacterial culture conditions and age, thus impeding identification. Another approach involves DNA amplification, which has excellent selectivity and parallel detection of several bacterial types. Without incubation, the sensitivity of DNA amplification is about 10 CFUs.

Accordingly, conventional techniques require long incubation times, costly consumables and skilled technical knowledge and labor. A rapid sensitive method of typing cells in a biological sample may be useful in the medical field where current laboratory techniques, even when performed at their most rapid pace, provide results that are 8-12 hours old.

SUMMARY

The invention provides a method and system to characterize cells. The methods and systems use selective enzymes that remove markers from the surface of cells that are characteristic of a cell-type or phenotype of the cell. The methods and systems use negative ionization (with ultra low-energy electrons) and mass spectroscopy to identify the cell marker and thereby identify and characterize a cell-type or phenotype.

The invention provides a method for characterization of bacteria through negative ionization and mass spectroscopy of their extracellular polysaccharides (XPSs). The method and systems are capable of rapid identification (e.g., less than 1 hour) and has single bacteria sensitivity and specificity from samples containing a variety of bacterial types.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

These and other aspects will now be described in detail with reference to the accompanying drawings, in which.

Like reference symbols in the various drawings indicate like elements.

DETAILED DESCRIPTION

Figure 1:
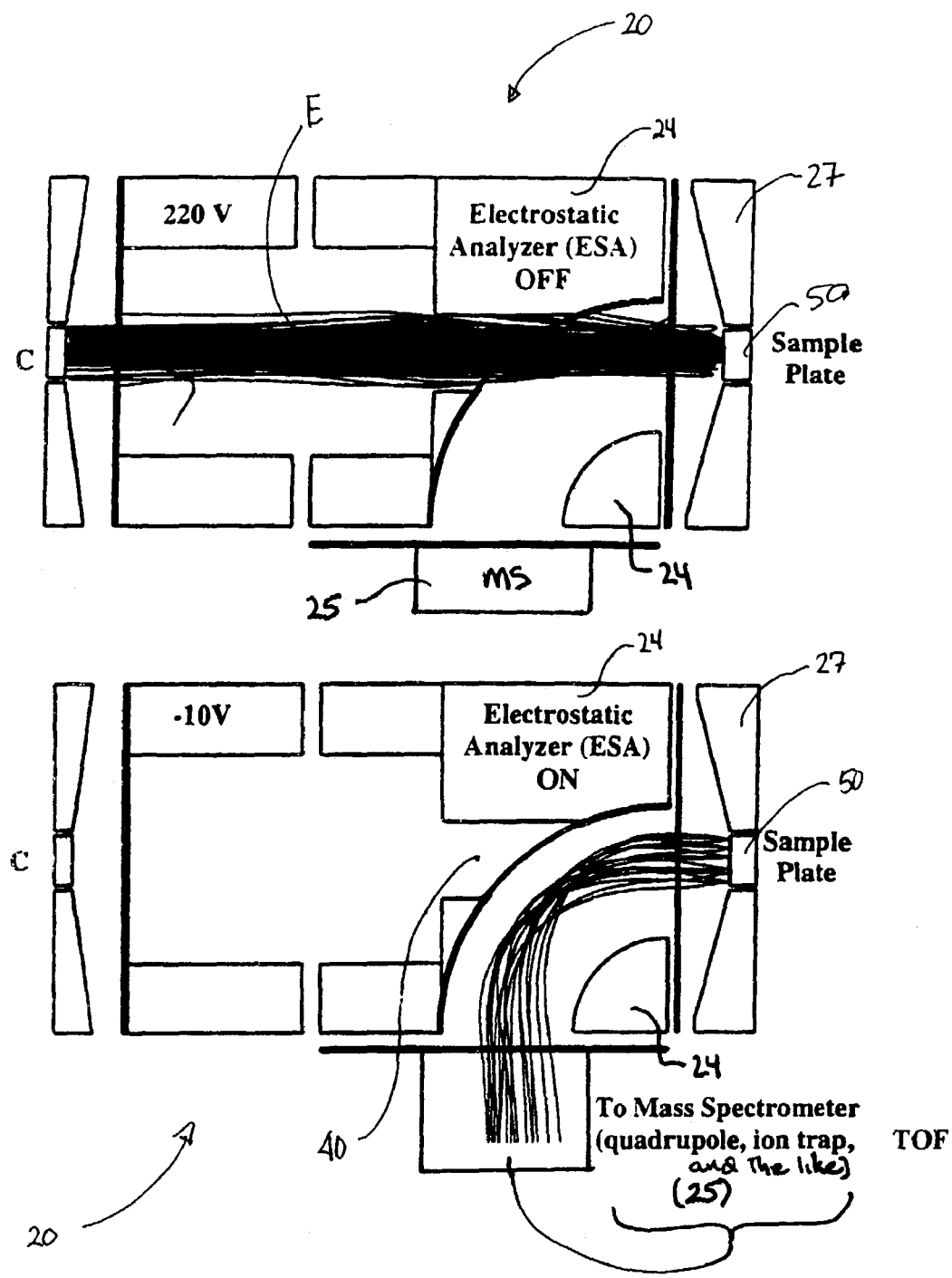
FIG. 1 depicts a schematic diagram of a low-energy ionization system for detecting and characterizing a cell, cell-type, or phenotype of a cell on a surface.

The invention provides methods and systems for the characterization of cells, cell-types, or phenotypes through the use of negative ionization and mass spectroscopy of extracellular surface markers. Cells applicable to the invention include both eukaryotic and prokaryotic cells. For example, the methods and systems of the invention are applicable to prokaryotic organisms such as bacteria including gram positive and gram-negative bacteria (e.g., *E. coli, S. typhimurium, Salmonella typhi, Vibrio cholerae, Vibrio harveyi, Yersinia pestis, Staphylococcus aureus, Streptococcus pyogenes, Enterococcus faecalis*, and *Bacillus subtilis*). Eukaryotic cells include, for example, mammalian cells and particularly human cells (e.g., normal and cancerous cell types).

As discussed herein, a phenotype includes observable characteristics of an organism including extracellular surface markers. Such observable characteristics are the result of selective expression corresponding to the cell's genotype. For example, many cells of different lineages in the human body express different cell surface markers characteristic of the particular lineage from which they are derived and/or cell surface markers characteristic of a particular tissue in which the cells are found. Any number of cell surface markers are applicable to the invention including, for example, oligosaccharides and polypeptides. Some specific, exemplary, markers are discussed herein, however, the invention is applicable to a broad range of cell surface markers.

A key to practical monitoring of small numbers of specific bacteria, for example, is the identification of a suitable biomolecule that can "mark" a given single-celled organism. The biomarker is ideally present in substantial quantities on a per-cell basis, as well as easily distinguished from the bulk of the cellular material by mass spectrometry.

The cells of many bacterial species specifically, gram-negative bacteria, are surrounded by a glycocalyx also referred to as a capsular polysaccharide ("CPS", cell surface carbohydrates) several hundred nanometers in thickness. The glycocalyx consists of a complex polysaccharide polymer that appears to be species specific. H. Geyer et al. "Degradation Of Bacterial Surface Carbohydrates By Virus-Associated Enzymes", Pure and Applied Chemistry, 55, pp. 673-85. These cell-surface carbohydrates are a logical choice for a near-term biomolecule for identifying bacterial cells. These carbohydrate polysaccharides typically comprise a minimum of several percent of dry cell weight, making them an ideal biomarker for detecting small numbers of a given bacteria.

Capsular and cell wall polysaccharides function as virulence factors by protecting bacterial from nonspecific host defenses such as complement and phagocytes. As type-specific antigens, they also serve as markers of infection and aids to serodiagnosis. In addition to the capsular and lipopolysaccharide antigens discussed here, many bacteria also produce other carbohydrate antigens such as teichoic acids, S-layer glycoproteins, and glycolipids.

Capsular polysaccharides are high molecular weight antigens ($10^5$ to $10^6$ daltons, Da) built from several thousand oligosaccharide-repeating units; typically these repeating units contain from one to six monosaccharide residues. Fungi and bacteria are capable of assembling an array (several hundred) of linear and branched polysaccharide structures that often incorporate rare monosaccharides, as well as noncarbohydrate substituents such as acetate or phosphate esters and pyruvate ketals. Examples of simple capsular polysaccharides are homopolymers (polymers composed of a single monosaccharide) such as those found on *Neisseria meningitidis* groups A, B, and C antigens. The B and C antigens are homopolymers of glycosidically linked sialic acid residues, while the A antigen typifies many capsular antigens in that it utilizes a phosphodiester to connect the repeating units, in this case a monosaccharide.

Some capsular antigens of *N. meningitidis* and group B Streptococcus resemble carbohydrate epitopes that occur on mammalian glycolipids and glycoproteins. For example, the polysialosyl antigen of group B meningococcus resembles glycan chains present on the fetal neural cell adhesion molecule (E)N-CAM. Oligosaccharide sequences that occur in the Group B streptococcal polysaccharides exhibit structural homology with human serum glycoproteins and glycolipids, since the capsular antigens of type Ia, Ib, II, and III possess the αDNeu5Ac(2→3)βD-Gal(1→4)βDGlcNAc epitope, found as terminal structures in glycopeptides and glycolipids. This mimicry is thought to allow the bacteria (as well as cancer cells) to evade the host's immunological system.

Lipopolysaccharides, such as the O-antigen and oligosaccharide core components, are major antigens of Gram-negative bacteria. The O-antigens resemble capsular antigens in having a repeating unit motif, but they possess even greater structural diversity. Certain bacteria such as *Haemophilus influenzae, Neisseria meningitidids,* and *N. gonorrhoeae* produce rought-type lipopolysaccharides (devoid of O-polysaccharide).

Similar to many bacteria, mammalian cells also include cell surface oligosaccharide epitopes. These macromolecules, which cover large areas of the cell surface, are located at the cell membrane with the carbohydrates protruding from cell's surface. Interactions between the carbohydrate, the lipid/protein, and the membrane surface may modulate the antigenic characteristics of certain oligosaccharide epitopes. For example, blood group antigens are the molecules expressed on the surface of human red blood cells (RBC). The most popular blood group antigens of clinical importance are the blood group ABO antigens and Rh antigens. Blood group antigens comprise a large number of molecular epitopes including polypeptides, glycoconjugates and glycoproteins. The human blood group A or B antigens are present on RBC as glycolipids and glycoproteins. The A-antigen and the B-antigen are trisaccharides, and the H antigen is a disaccharide, which is the backbone of A/B trisaccharides. The ABO blood group antigens are found on glandular epithelial cells and other epithelial cells, as well as endothelial cells.

Lewis A and Lewis B antigens are blood group antigens related to blood group ABO antigens. Lewis A antigen was first recognized by an antibody in a serum sample from Mrs. H. G. D. Lewis. The Lewis antigens ($Le^a$ and $Le^b$) of erythrocytes are not synthesized in hematopoietic tissue of mature erythrocytes but instead are incorporated into the red cell membrane from serum. The abnormal expression of the sialylated form of the Lewis A antigen (Sialyl $Le^a$ (Lewis a)) is closely correlated with various forms of cancer including pancreatic cancer, gallbladder/bile duct cancer and cholangiocarcinoma. A monoclonal antibody CA19-9 against sialyl $Le^a$ is currently used to diagnose these tumors. Lewis X antigen and its sialylated form (sialyl $Le^x$ antigen) are not blood group antigens but their structure is related to Lewis blood group antigens. The stage-specific embryonic antigens (SSEA-1) is the $Le^x$ antigen. The sialyl $Le^x$ is known as a receptor of E-selectin and is important in lymphocyte homing.

Accordingly, certain gangliosides are important in pathogenic processes. Some, such as $GD_3$ and $GD_2$, occur as tumor-associated carbohydrate antigens, and fucosylated structures related to the Lewis antigens have been identified as oncofetal antigens (e.g., di- and trimeric forms of $Le^x$). The $Le^x$ structure bearing a Neu5Ac residue at the O-3 atom of galactose, sialyl Lewis x, is a specific ligand for members of the selectin family of cell adhesion molecules, which are involved in inflammation. Cholera toxin from *vibrio cholerae* binds to $GM_1$, while tetanus and boulinum toxins, both of which block neurotransmitter release, bind to the major neuronal gangliosides $GT_{1b}$ and $GD_{1b}$.

Other surface molecules useful in characterizing a cell type include cell surface polypeptides. Such polypeptides include cell surface ligand binding polypeptides (e.g., cell surface receptors and the like). Many such polypeptides are expressed selectively on certain types of cancer cells.

Detecting specific carbohydrate or polypeptide molecules on a cell can be used to determine the type of cell present in a sample. Current methods utilize antibodies that specifically bind to polypeptides or use chromatography techniques to detect a particular carbohydrate molecule. These methods are time consuming and often render the cell or sample unviable thus limiting further study (if needed).

The sample comprising the cell to be detected is first treated or contacted with an agent that provides the biomolecule to be detectable in an ionizable fashion by releasing the biomolecule (e.g., the cell surface marker) from the cell while keeping the cell structure viable and intact. Methods and compositions for releasing the cell surface marker are provided herein.

Enzymes can be used to remove cell surface markers such as carbohydrates and/or polypeptides from the surface of cells without damaging the cell itself. The removed carbohydrate and/or polypeptide can then be ionized and analyzed. Because the cells are still viable, the cells can be cultured and subjected to additional assays as needed or desired.

Enzymes useful for cleaving cell surface carbohydrates and/or polypeptides are known in the art. Where a cell marker is known a desired enzyme can be designed or selected from a catalog of known enzymes. A list of known enzymes is provided on the world wide web at URL: us.expasy.org/enzyme/.

Bacteriophages are an excellent source of enzymes for use in identifying bacterial cells. Bacteriophages are viruses that infect bacteria. The viruses that infect bacteria encapsulated by a glycocalyx are specially adapted to penetrate the polysaccharide barrier. The tail fibers or spikes by which these viruses are seen to attach to bacteria contain enzymes—generally referred to as endoglycanases or endopolysaccharases—that degrade the glycocalyx. These enzymes exhibit a high degree of substrate specificity. For example, a strain *Klebsiella pneumoniae* produces a capsular polysaccharide known as K63. A phage ("K63 phage") is capable of specifically degrading this same polysaccharide. The K63 CPS is a straight chain heteropolymer of fucose, galacuronic acid and galactose linked, in that order, by a 1-3 glycosidic linkages. The K63 phage enzymatically hydrolyzes the a 1-3 linkage between the galactose and fucose monomers.

Bacteriophages are ideal because they produce a polysaccharide-degrading enzyme (endoglycanase), which is specific to the polysaccharide produced by the strain that the bacteriophage infects. This specificity equals that of antibodies, and has in fact been used in medical laboratories as an alternative to antibody serotyping of bacterial strains.

Exposure of bacterial to dilute solutions of phage-bearing endoglycanase and purified endoglycanase leads to rapid removal of the XPS from the cell surface. Microscopic observation shows that the process is essentially completed in less than two minutes at room temperature in distilled water. The cell surface polysaccharide that is released is subsequently slowly degraded to its basic oligosaccharide repeat unit over the course of hours. A single bacteria's extracellular polysaccharides are typically comprised of 1.2 million polysaccharide chains of at most 3 or 4 different types. This means that a reasonable chance of detection in a mass spectrometer exists if the polysaccharides from only one bacterium are available. This in turn implies that a lower limit of detection can be one bacterium on a metal surface. The typical mass of a polysaccharide chain is on the order $10^3$ Da. Mass spectrometry utilizing conventional ion trap mass spectrometers can characterize these chains to a mass accuracy of less than 1 Da.

Methods and systems for determining a cell type or phenotype are provided herein. The methods and systems use techniques based on positive or negative ion formation via charge transfer to a biological or target molecule (i.e., a cell surface oligosaccharide or polypeptide), or electron capture under multi-collision conditions in a Maxwellian distribution of electron energies (with a peak at about 40 millielectron volts (meV)) at the source temperature (300 K). Such techniques include atmospheric sampling, glow-discharge ionization (ASGDI), atmospheric pressure ionization (API), electron capture detection (ECD), and negative-ion chemical ionization (NICI).

In order to maximize ion formation, and therefore molecule detection sensitivity, high electron currents at low energies (<10 meV) are needed at the point of attachment between electrons and the molecules to be detected (e.g., cell surface markers). To provide a better "match" between the electron energy distribution function and the attachment cross section, an electron reversal technique is used. In this technique, electrons are brought to a momentary halt by reversing their direction with electrostatic fields. At a reversal region R, the electrons have zero or near-zero energy. The reversal region is in contact with and/or encompasses a biological sample comprising a cell and/or a molecule associated with a marker of a cell to be determined. Molecules to be detected (e.g., cell surface markers) associated with the cell type thereby come into contact with the electrons and the zero or near-zero energy electrons attach to the molecules. Slowing the electrons to subthermal (<10 meV) energies is ideal because the cross section for attachment of several large classes of molecules (e.g., cell surface markers) is known to increase to values larger than $10^{12}$ cm$^2$ at near-zero electron energies. In fact, in the limit of zero energy, these cross sections are predicted to diverge as $\epsilon^{-1/2}$, where $\epsilon$ is the electron energy. This is known as the quantum mechanical Wigner s-wave threshold law.

Accordingly, negative-ion formation at ultralow energies (less than 0.1 eV) can occur with extremely high attachment probability (cross section). This immediately correlates to a high detection sensitivity when a very low-energy electron strikes, for example, a cell surface marker. The "gentle" ionization (i.e., non-fragmenting, or causing minimum dissociation of the target) is used to characterize the heavy molecular-weight cell surface markers (e.g., extracellular polysaccharides). This prevents production of a "forest" of mass-spectral features, either from fragmentation of the target molecule or destruction of the cell wall, which would wash out a particular cell surface marker fingerprint. A cell surface marker contains radicals having high electron affinity (such as $NH_2$, $NH_2$—C=O, O—C=O, or O—P=O groups). Attachment can then take place to produce one or more negative-ion fragments of the cell surface marker constituting the marker on the specific cell type to be detected.

As used herein, a biological sample includes material or compositions comprising cells, cell fragments, or cell free compositions derived from a biological sample. For example, in one aspect of the invention a biological sample comprises a cell(s) to be identified. In another aspect of the invention, the sample comprises cells to be identified that have been contacted with an enzyme or enzymes capable of cleaving a cell surface marker from the cell(s) to be identified. In yet another aspect, the invention provides a biological sample comprising a cell-free extract comprising cell surface markers or expressed polypeptides indicative of a cell type.

The methods and systems described herein have applicability to the detection of a broad range of cell surface markers. These include, for example, oligosaccharides and polypeptides, including markers on prokaryotic cells and mammalian cells. Such applicability has utility in identifying cells in medical diagnostics and in environmental sampling (e.g., food monitoring, quality-assurance in pharmaceuticals, and the like).

In the invention, the reversal region R is matched to the shape of the biological sample surface using a three-dimensional fields-and-trajectories calculation with full accounting of electron and ion space charge. "Matched," as used herein, means that the shape of the electrostatic field at the reversal region is adjusted to increase the number of electrons reflected back to the cathode, with the electrons having a low axial and radial energy over the entire sample surface. This increases the number of reflected electrons in the reversal region and hence increases the opportunities for ion formation by the molecule of interest. In this regard, a dramatic increase in detection sensitivity for classes of zero electron-energy attaching molecules is provided.

This ionizer system comprises a source of electrons, which may be from, for example, a directly or indirectly-heated cathode (of any geometric shape), or a field-emission source. An An electron-optics lens system extracts and focuses the electron beam onto an electrostatic mirror, which slows the electrons contained in the beam to zero- or near-zero electron energies. Each band of energies from the cathode source will be stopped at a different plane in this mirror thereby providing a plurality of stacked planes of zero-energy electrons. A biological sample comprising a cell and/or molecule to be identified is located at a region where the electrons are reflected and hence have a zero or near-zero energy. The biological sample is prepared and located in the region of zero electron energy and the zero or near-zero energy electrons will attach to the molecules (e.g., cell surface markers) in the biological sample and form a characteristic negative-ion spectrum ("fingerprint") of the molecule. This spectrum is analyzed by a subsequent mass spectrometer.

The method and apparatus are particularly useful for detecting molecules (e.g., cell surface molecules) that possess a large efficiency (cross section) for attaching the zero-energy electrons. As discussed above, molecules include cell surface oligosaccharides and/or polypeptides present on the surface of the cell(s) in a biological sample. The cell surface molecules are ideally cleaved or removed from the intact cell by a chemical agent such as, for example, an enzyme or plurality of enzymes. Accordingly, the method and apparatus are useful for detecting a molecule associated with a particular cell type and thereby identify a cell associated with that molecule.

If the molecule attaches to a higher-energy electron, then the electrostatic potential on the mirror electrode can be weakened, so that a higher-energy electron beam impinges on the sample, and attachment occurs at those energies. The electron attachment and ion extraction are carried out in a pulsed mode: (a) the electron beam is pulsed "on," and attachment takes place; (b) the electron beam is pulsed "off," and the subsequent ion optics are pulsed "on" to extract and focus the negative ions onto the entrance aperture of the mass analyzer. This analyzer can be of any type adequate to provide the needed sensitivity mass range and resolution. This includes, but is not limited to, a quadrupole, ion-trap, magnetic sector, time-of-flight, and/or trochoidal analyzer. Miniaturization of the entire system (e.g., optics and electronics) is also feasible, and is considered part of the invention. The attachment cross section of a molecule is known to be large at zero electron energy and almost certainly has an "s-wave" dependence in which the attachment cross section is proportional to $\epsilon^{-1/2}$.

In general, molecules that have an extremely large cross section for attaching zero-energy electrons have a cross section that varies as (electron energy)$^{-1/2}$. Hence, the attachment rate (or ionization efficiency) is favored for slow electrons. For molecules that attach higher-energy electrons, the mirror can be weakened to generate faster electrons at the point of attachment to the target molecule.

Referring to FIG. 1, a sensor apparatus for detecting molecules and identifying a cell type or phenotype of a cell is shown. A biological sample (50) comprising a cell or cells to be identified having one or more cell surface markers is introduced into a sensor ionizer, also referred to as an electron-ion optics system 20, such that the biological sample comprising a molecules comes into contact with a low energy electron beam in the optics system 20. With reference to FIG. 1, the electrons contact the biological sample (50), which may contain a target molecule (e.g., a cell surface marker). Negative ions may be formed by the electron dissociative attachment process.

This so-called Biological Reversal Electron Attachment Detector (BioREAD) is a pulsed device. In the first half of the cycle electrons are reflected in the electrostatic mirror and negative ions are formed in the attachment region (50). In the second half of the cycle, the negative ions are extracted from the attachment region and are deflected and focused by an electrostatic analyzer (ESA) 24 into a quadrupole mass spectrometer (QMS) 25. The electron-ion optics system 20, the ESA 24, and mass analyzer 25 may be enclosed in a vacuum chamber 26.

Any type of mass analyzer may be adapted to the invention, including variable dispersion mass spectrometer as described in PCT publication number WO89/12315, a time-of-flight mass spectrometer, a magnetic-sector mass spectrometer, an ion trap, and a quadrupole mass spectrometer, to name but a few. The quadrupole mass analyzer (QMS) 25 typically comprises four rod electrodes placed parallel to and symmetrically around a center axis with a pair of non-conductive holders for holding the electrodes at both ends of the four rod electrodes and a pair of plates for clamping the non-conductive holders (see for example, U.S. Pat. No. 5,459,315).

In order to effect "perfect" electron reversals at the surface containing the biological sample (50) and still extract the resulting ions (e.g., negative ions) a folded electron-ion beam geometry is used. The ESA provides for this capability. The negative ions formed near the surface of the biological sample (50) are extracted with a pulsed voltage and focused into the ESA, which deflects the ions into successive ion optics for focusing into a mass spectrometer.

The mass spectrum of the negative ions is a unique fingerprint of the particular species present in a biological sample (e.g., a specific cell surface marker oligosaccharide or polypeptide). Due to the potentials applied to the lens elements in the first half of the BioREAD cycle, positive ions formed in the attachment region are extracted and focused into the electrostatic analyzer (ESA) 24, which deflects them away from entering the mass spectrometer. The ESA therefore provides an additional method to differentiate the negative and positive ions produced in the BioREAD. If the positive and negative ions are not differentiated, the mass spectrum will no longer be a simple fingerprint of the species of interest.

Figure 2:
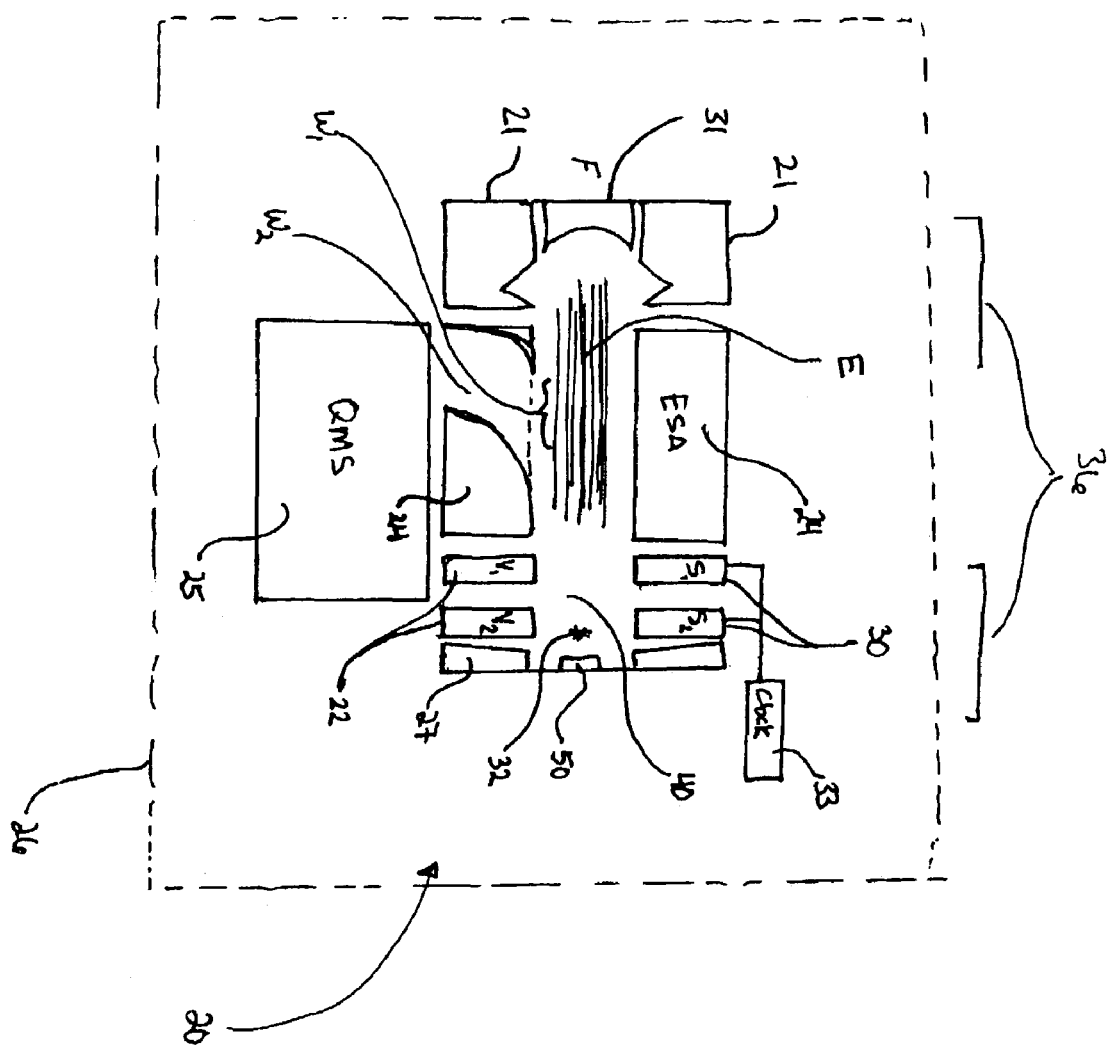
FIG. 2 depicts a schematic representation of an electron-ion optics system and mass spectrometer.

Referring to FIG. 2, the electron-ion optics system 20 includes a cathode (F) and electron extractor component 21, one or more reversal components 22, an ion extraction component 27, MOSFET switches 30 and a clock controlling the MOSFET switches 33. The MOSFET switches are operationally associated with the cathode component 21, the reversal component 22 and the ion extraction component 27. The cathode component 21 includes an electron emitter (31, F) such as a directly-heated cathode or indirectly-heated oxide dispenser cathode. The electron source (i.e., electron emitter or cathode) 31 emits electrons (E) that are focused into the reversal component 22. The design of the electron emitter can include the use of Child's Law to determine the spatial width of the cathode. The concave face of the cathode can be designed with a radius of curvature r such that 2r is greater than that width. While decreasing the radius of curvature to half the cathode width will result in a true hemispherical surface for maximum electron emission, electrons emitted near the edge of the hemisphere will have an initial direction of motion perpendicular to the axis of the focusing and accelerating lens elements, which will tend to interfere with the desired shape of the beam being formed.

The reversal component functions as an electrostatic mirror to reduce or neutralize the kinetic energy of the electrons at the reversal (R) position 32. The reversal component is comprised of electrodes that create electric fields. The electric fields act as lenses that modify the electron velocity by reducing it to zero or near-zero. The electrodes $V_1$ and $V_2$ comprising the reversal component may be a conductive metal or any material suitable for such use. The electron source and reversal component comprise a lens stack 36 separated by the ESA 24. The geometry of the elements comprising the lens stack are shaped to provide a reversal region that is matched to the shape of the electron emitter. This is accomplished by computer-analyzing electron trajectories at the equipotential surfaces of the reversal component. The equipotentials at the cathode of the method are not converted into planar equipotentials by straightening them into parallel electric-field configurations. In the present system, potentials are maintained throughout the system (i.e., from cathode to reversal region). Fields and trajectories are computed using a three-dimensional fields-and-trajectories calculation with full accounting of electron and ion space charge. Typically the calculation is a component of computer code. The quality of the reversed electrons at the position R (i.e., how close their velocity in the radial and axial directions is reduced to zero), is monitored as a function of lens stack geometries that includes lens positions, lens shapes, and the degree of space charge in the electron beam. The monitoring is accomplished by querying the computer code for these quantities at the location R.

The electron beam is square-wave modulated by fast switches $S_1$-$S_2$ with a nearly 50% duty cycle. These switches are power MOSFET-based to ensure fast (50 ns) rise times between full-floating lens voltage. Electron attachment to the molecules in the biological sample takes place at the reversal plane R (32) during that half of the duty cycle when the electron beam is "ON". The resulting negative ions are extracted during the second half of the duty cycle (electron beam is "OFF") and focused by ion extraction component 27 onto the entrance plane ($W_1$) of a electrostatic analyzer (ESA) 24. The extracted ions are then deflected by the ESA 24 to ensure the sign of charge, and further focused onto the entrance plane ($W_2$) of quadrupole mass analyzer (QMS) 25.

Electrons are generated at the electrode F and accelerated into the reversal region R where attachment or dissociative attachment (DA) to molecules in the biological sample takes place. Fast switches $S_1$-$S_2$ pulse electrons on during one-half cycle, then pulse negative ions out towards the electrostatic analyzer 24 during the second half. Ions selected by the ESA are focused into the QMS and individual masses are scanned and detected.

In one embodiment, a device for shielding the entrance $W_2$ contained within ESA 24 is provided (depicted in FIG. 2 by dotted line). The ESA provides a means of differentiating negative and positive ions by acting as an electron energy filter. Such filter may be any electrostatic or electromagnetic energy analyzer configured for the application, for example being a cylindrical electrostatic analyzer, or a hemispherical electrostatic analyzer.

Figure 3A:
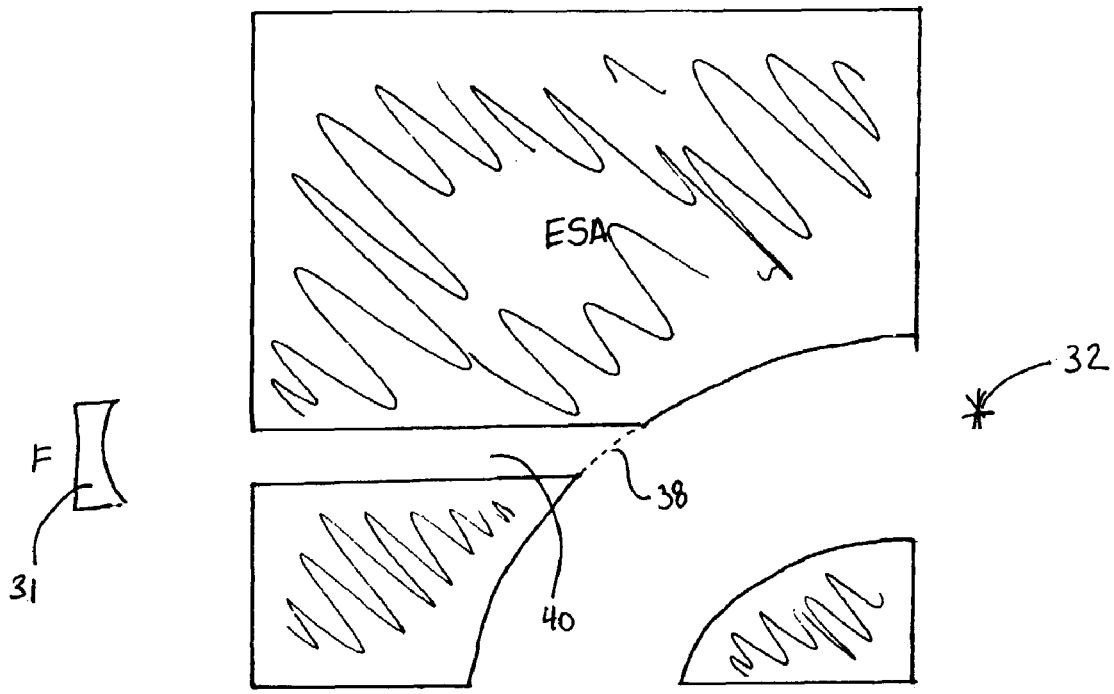
FIG. 3A and FIG. 3B depict enhanced views of the electrostatic analyzer (ESA) inner and outer spheres, and the aperture located in direct line-of-sight of the emitter F. A device that maintains the integrity of the electric field shields (covers) the aperture and inhibits the deposition of non-conductive substances.
Figure 3B:
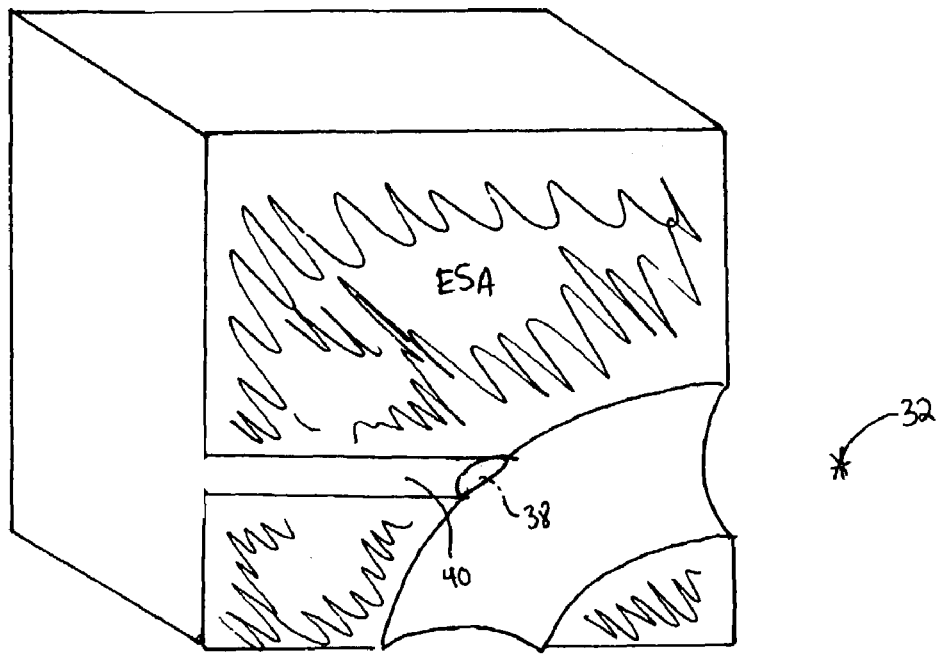

Negative ions formed at the reversal region are focused by the ESA 24. However, due to the potentials applied to the lens elements in the first half of the BioREAD cycle, positive ions formed in the attachment region are extracted and focused into the ESA 24 as well. The ESA deflects the unwanted positive ions away from entering the mass spectrometer. Referring generally to FIG. 3A and FIG. 3B, studies have determined that the outer surface of the ESA at position 38, which is in the line-of-sight of the electron emitter F, is susceptible to contamination with non-conductive material. The non-conductive material results from the decomposition of the constituents present in the sample. Such decomposition is attributable to charging of the outer radius of the ESA elements by positive ions.

In order to reduce the surface-charging effects of the ESA and inhibit the deposition of non-conductive contaminants within the apparatus, a device 38 (FIG. 3A and FIG. 3B) which resides on the outer sphere of the ESA and is in the direct line-of-sight of the electron emitter F, is provided. The device 38, while maintaining the integrity of the electrostatic field, presents a reduced surface area at the critical region of the ESA most susceptible to contamination. The device is composed of any material that shields the entrance to the aperture 40 but does not disrupt the passage of negative ions through the ESA 24. Further, the device is composed of any material that does not completely prevent the egress of positive ions from the ESA through aperture 40. The device is positioned at the entrance of aperture 40. Aperture 40 provides a channel integrally-associated with the ESA through which positive ions exit the ESA. The device can be removable or non-removable from the ESA.

A device 38 positioned at the entrance of aperture 40 can be a conducting mesh, screen, membrane or any porous material that provides a plurality of openings forming a non-solid surface on the outer sphere of the ESA and in the direct line-of-sight of the electron emitter F. The device will present less than 100% solid surface area in the critical region. For example, the device can present about 10% of a solid surface area at the critical region, thus reducing by about 90% the material to be coated by contaminants. It is understood that any amount of solid surface that is less than 100% solid at the indicated position and is sufficient to maintain the integrity of the ESA electrostatic field is encompassed by the invention.

Figure 4:
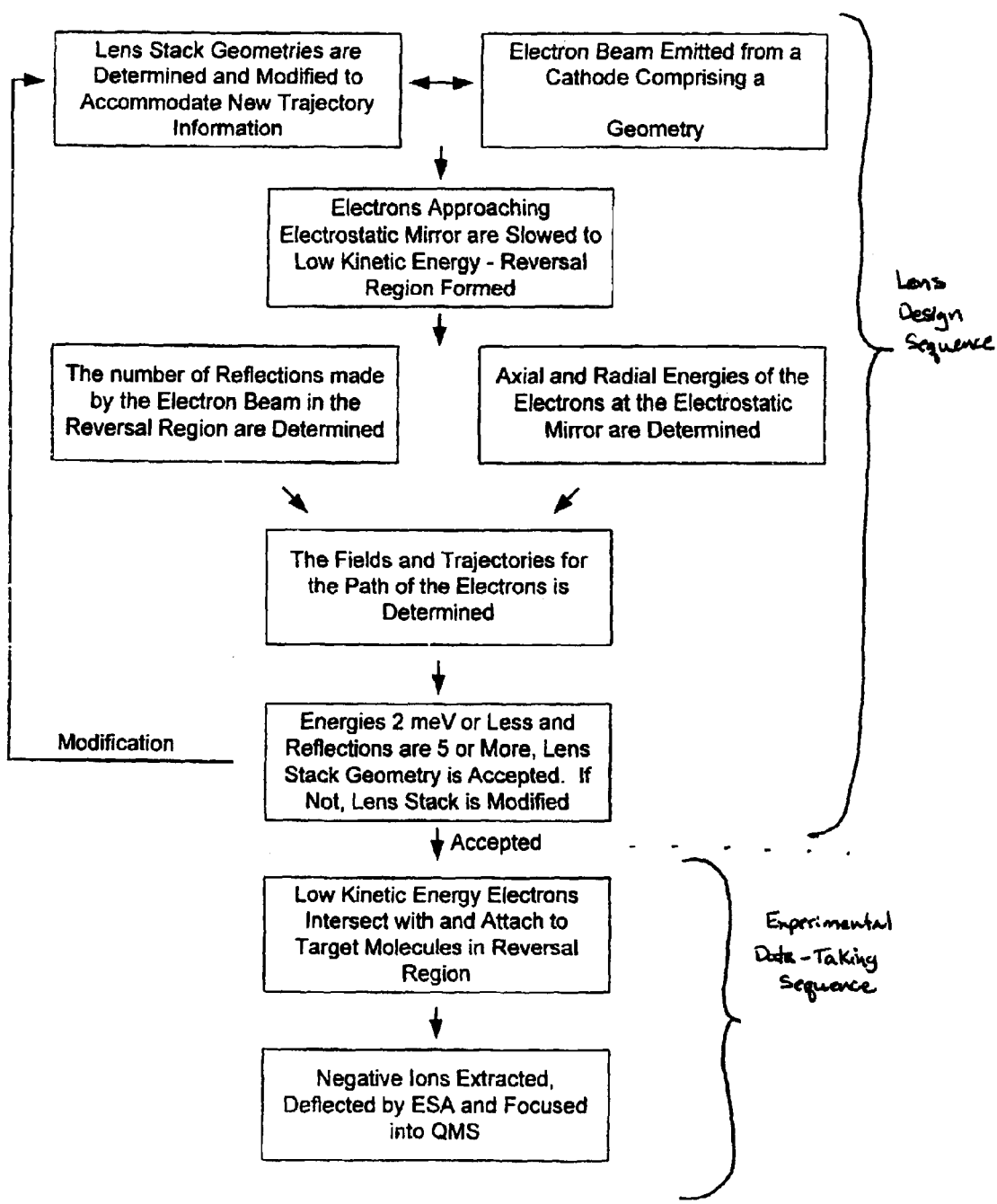
FIG. 4 depicts a flow diagram of an exemplary method for designing the low-energy ionizer and electron-ion optics system for determining a cell type of phenotype of a cell.

Referring generally to FIG. 4, lens stack geometries are initially determined and subsequently modified to accommodate electron trajectory information so that electron reversals are matched to the electron emissions. The electron trajectory can be determined analytically from the results of the axial and radial kinetic energies of the electrons at the reversal region R. The axial and radial electron kinetic energies are obtained from the computation itself. Alternatively, the electron trajectories can be examined visually by specifically noting the number of reflections the electron beam makes in the reversal region. If the electron energies calculated at the reversal region R are less than 2 meV, and the number of reflections the electron beam makes in the reversal region is more than 5, then the geometry of the lens stack is accepted as optimized. The entire lens stack geometry is to be matched to the electron emitter geometry. Thus, the entire lens geometry (optics and sample surface) is considered during the computer fields and trajectories analysis.

The lens stack geometry (i.e., the shape and positions of the elements determine the electron and ion focal properties) is initially determined and subsequently modified so that it is matched to the geometry of the electron emitter.

The space-charge distribution of the electron beam and lens geometries can be determined by calculations or computer codes. A means for determining the fields and trajectories for the electrons in an electric-field configuration includes any means known to the skilled artisan. For example, the Herrmannsfeldt field and trajectory code can be used to calculate electron trajectories. Additional codes include, but are not limited to, the MEBS code (Munro Electron Beam Software), MAFIA code and VECTOR FIELDS code.

As the electrons approach the reversal region, they are slowed and their kinetic energy is reduced to a few millielectron volts. Their energy becomes almost entirely potential energy. Sample molecules present in the biological sample contact the region of low energy electrons. Accordingly, electrons emitted from electron source 31 having a particular energy are decelerated by the reversal component (e.g., electrostatic mirror) 22 to a zero, or near-zero, longitudinal and radial velocities at the reversal plane. The electrons emitted from the electron source have a Boltzman distribution of kinetic energy with a mean energy of about 0.25 electron volts. The region of electron reversals at the electrostatic mirror is comprised of a spatial extent of stacked reversal planes along the axis of the lens system. For example, the electrons with low kinetic energy will reverse before those electrons with higher kinetic energy.

The electrostatic mirror is designed to facilitate an intersection between the spatial extent of the reversal planes and the spatial extent of the target molecular surface, thereby providing enhanced spatial overlap between the slowed or stopped electrons and the molecules present in a biological sample. The enhanced spatial overlap increases the efficiency of electron attachment to the target molecules. Therefore, an electrostatic mirror of the invention is designed to avoid placing large voltage potentials on the electrostatic mirror because a sharp reversal region will form. This sharp reversal region will be spatially-narrow in extent such that a less than optimal spatial overlap with the target beam will occur. Similarly, the electrostatic mirror is designed to avoid low voltage potentials or the electrostatic mirror. Such potentials spread the reversal planes out in space which encourages 1) poor reversals packets for high electron currents (packets are of too high a radical energy), and 2) larger planes in a spatial extent than the target beam, hence providing less than optimal overlap or ionization efficiency.

Subsequent to reversal at the electrostatic mirror, the electrons, which did not undergo attachment to a target molecule present in a biological sample, are reflected backwards, and travel in the opposite direction through the electrostatic lens systems. The present apparatus provides a mechanism for confining and focusing these "backward" trajectories such that their effect is included in the trajectories of the forward-going electron trajectories entering the reversal region.

The geometries of the cathode component and of the lens stack are communicated to a computer comprising software. The software optimizes the geometry of the lens stack with respect to the cathode component. Modifications in the electron emission profile necessitates a modification in the geometries of the components of the lens stack in order to enhance the interaction between electrons with low kinetic energy and the target molecules present in the gas beam which traverse the reversal region (R) (FIG. 1 and FIG. 2). Electron paths are calculated in an electric-field configuration (e.g., as equipotentials). In contrast to previous chemical detection systems, trajectories are not linearized into a parallel electric-field configurations. Thus, any means to more precisely identify the quantity of electron reversals occurring in the reversal region is provided.

In U.S. Pat. No. 5,374,828 ('828), electron trajectories had to be calculated (because of computer memory considerations) by dividing the system into two parts: part 1 included the electrodes 11, 11', 12, 13, 14; and part 2 the electrodes 12-17 (see FIG. 1 of the '828 patent). Three electrodes 13-15 were made common to both parts so that fringing fields from part 1 were included in part 2. After determining the electron trajectories for part 1, the output trajectories were injected (as initial conditions) into part 2 at a position on the lens axis where the potential was identical in both parts. While adequate, the partitioning of electron trajectories and subsequently piecing them back together is inherently less precise than the method presented herein: the accumulated errors over 5-10 reversal cycles can lead to miscalculated trajectories.

Thus, the geometry of the elements comprising the lens stack are shaped to provide a reversal region that is matched to the shape of the electron emitter. Small spherically-shaped tips may be included on lens elements $V_1$ and $V_2$ (see FIG. 2, 22) are examples of how the lens stack can be optimized to accommodate the extraction technique by analyzing electron trajectories at the equipotential surfaces of the reversal component. Once the initial analysis is complete, the lens stack is modified to match the geometry of the electron source. As previously noted, the geometries of the elements of the lens stack are optimized with respect to the electron emitter. The optimization is concurrent because any modification in the electron emission profile necessitates a modification in the shape of the mirror. The two portions of the electrostatic lens systems, the electron source and the electrostatic mirror, comprise a coupled system. Optimum attachment efficiency of the systems arises from ensuring that there are multiple passes of the electron beam between the reversal region and the cathode, and near-zero or zero energy at the sample surface. The effect is to maximize the electron attachment efficiency. The system couples an electron source with a lens system comprising an electrostatic mirror. The electron source and lens system are concurrently modulated such that fields-and-trajectories codes are not limited to modeling only the trajectory a single packet of electron current emitted from the electron source. Accordingly, multiple reversals are observed in the code as a segment of electron charge shuttling between the cathode and reversal regions of the coupled lens systems.

For example, referring generally to FIG. 2, the electron source 31 can comprise a directly-heated, cathode from which electrons are extracted and accelerated by a lens system. They are then focused into an electrostatic mirror. The mirror decelerates the electron beam to zero longitudinal velocity and near-zero radial velocity at the reversal plane R. At R, the reversed electron beam crosses or "intersects" the molecular target surface. Negative ions formed at R by the attachment or dissociative attachment (DA) process are then extracted by element 27.

The physical description of the computer simulation is that of a coupled lens system focusing and reversing continuously-emitted electron current over a distinct period of time. The design of the optical system ensures that high quality reversals are still effected with the inclusion of successive electrons being injected into the system.

The negative ions generated upon contact with a biological sample are focused into a mass analyzer. The negative ions form a fingerprint of molecules present in the biological sample. For example, the negative ion of a cell surface polysaccharide produces a negative ion pattern associated with that particular polysaccharide. By profiling of known cell surface molecules, a database correlating molecules and negative ion mass spectrum is generated. Unknown molecules may then be characterized or identified using pattern comparison and recognition algorithms.

The analysis of a negative ion pattern (e.g. a fingerprint) may be implemented in hardware or software, or a combination of both (e.g., programmable logic arrays or digital signal processors). Unless otherwise specified, the algorithms included as part of the invention are not inherently related to any particular computer or other apparatus.

In particular, various general purpose machines may be used with programs written in accordance with the teachings herein, or it may be more convenient to construct more specialized apparatus to perform the operations. However, preferably, the embodiment is implemented in one or more computer programs executing on programmable systems each comprising at least one processor, at least one data storage system (including volatile and non-volatile memory and/or storage elements), at least one input device, and at least one output device. The program code is executed on the processors to perform the functions described herein.

Each such program may be implemented in any desired computer language (including machine, assembly, high level procedural, or object oriented programming languages) to communicate with a computer system. In any case, the language may be a compiled or interpreted language.

Each such computer program is preferably stored on a storage media or device (e.g., ROM, CD-ROM, or magnetic or optical media) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A number of embodiments of the invention have been described. Nevertheless, it will be understood that various modifications may be made without departing from the spirit and scope of the invention. Accordingly, other embodiments are within the scope of the following claims.

What is claimed is:

1. A method of identifying a cell in a non-gaseous sample, comprising:
    contacting the non-gaseous sample on a sample plate with at least one enzyme specific for a cell surface marker, such that the enzyme cleaves the cell surface marker from the cell surface;
    focusing electrons emitted from an electron source in a direction towards a reversal region that comprises the sample plate and an electrostatic mirror to slow down the electrons to zero- or near zero energies;
    controlling an electric field distribution to match the reversal region to the shape of a surface of the non-gaseous sample on the sample plate, based on a three-dimensional fields-and-trajectories calculation, to cause contacting of the non-gaseous sample on the sample plate with the electrons of zero- or near-zero energies to generate, at the sample plate, ions that include at least negative ions at the cell surface marker;
    separating negative ions from the generated ions and detecting a pattern of said negative ions;
    comparing the pattern of detected negative ions to a library comprising fingerprints of ions associated with types of cells;
    using a match with a member in the library to identify the cell in the non-gaseous sample.

2. The method of claim 1, wherein the cell is a prokaryotic cell.

3. The method of claim 2, wherein the prokaryotic cell is a bacterial cell.

4. The method of claim 3, wherein the type of cell comprises a genus, species, and/or strain of bacterial cell.

5. The method of claim 3, wherein the cell surface marker is a carbohydrate antigen.

6. The method of claim 5, wherein the carbohydrate antigen is a capsular/cell wall polysaccharide.

7. The method of claim 5, wherein the at least one enzyme is an endoglycanase.

8. The method of claim 1, wherein the cell is a eukaryotic cell.

9. The method of claim 8, wherein the cell is a mammalian cell.

10. The method of claim 9, wherein the cell surface marker is a cell surface polypeptide, carbohydrate, or a combination thereof.

11. The method of claim 10, wherein the enzyme is a protease.

12. The method as in claim 1, wherein the separating and detecting step further comprises:
    extracting and deflecting positive ions from the generated ions, and
    differentiating positive and negative ions, such that only negative ions are detected.

13. The method of claim 1, wherein the matching comprises adjusting a shape of electrostatic field at the reversal region to increase a number of electrons reflected back to the electron source, with the electrons having a low axial and radial energy over the entire sample surface.

* * * * *

UNITED STATES PATENT AND TRADEMARK OFFICE
CERTIFICATE OF CORRECTION

PATENT NO. : 8,116,981 B2
APPLICATION NO. : 10/447674
DATED : February 14, 2012
INVENTOR(S) : Ara Chutjian et al.

It is certified that error appears in the above-identified patent and that said Letters Patent is hereby corrected as shown below:

Title page, item (56), in Column 2, Line 5, under "OTHER PUBLICATIONS", delete "Chromotography," and insert -- Chromatography, --, therefor.

Title page, item (56), in Column 2, Line 10, under "OTHER PUBLICATIONS", delete "ionizaiton," and insert -- ionization, --, therefor.

Title page, item (56), in Column 2, Line 12, under "OTHER PUBLICATIONS", delete "Pinnaduwage et al. et al., "Enchanced" and insert -- Pinnaduwage et al., "Enhanced --, therefor.

In Column 1, line 13, please insert the following paragraph:

-- STATEMENT REGARDING FEDERALLY SPONSORED RESEARCH OR DEVELOPMENT
    The invention described herein was made in the performance of work under a NASA contract, and is subject to the provisions of Public Law 96-517 (35 USC 202) in which the Contractor has elected to retain title. --.

In Column 1, Line 16, delete "and," and insert -- and --, therefor.

In Column 4, Line 1, delete "meningitidids," and insert -- meningitidis, --, therefor.

In Column 4, Line 2, delete "rought-type" and insert -- rough-type --, therefor.

In Column 4, Line 50, delete "boulinum" and insert -- botulinum --, therefor.

In Column 5, Line 31, delete "the a" and insert -- a --, therefor.

In Column 6, Line 20, delete "$10^{12}$ cm$^{2}$" and insert -- $10^{-12}$ cm$^2$ --, therefor.

Signed and Sealed this
Twenty-ninth Day of May, 2012

David J. Kappos
*Director of the United States Patent and Trademark Office*

CERTIFICATE OF CORRECTION (continued)
U.S. Pat. No. 8,116,981 B2

In Column 7, Line 10, delete "An An electron-optics" and insert -- An electron-optics --, therefor.

In Column 9, Line 40, delete "a electrostatic" and insert -- an electrostatic --, therefor.

In Column 11, Line 10, delete "Boltzman" and insert -- Boltzmann --, therefor.

In Column 11, Line 30, delete "or" and insert -- on --, therefor.

In Column 11, Line 33, delete "radical" and insert -- radial --, therefor.